United States Patent [19]

Weissman

[11] 4,182,615
[45] Jan. 8, 1980

[54] DENTAL MODEL TRIMMER

[75] Inventor: Bernard Weissman, New York, N.Y.

[73] Assignee: Ipco Hospital Supply Corporation, White Plains, N.Y.

[21] Appl. No.: 867,166

[22] Filed: Jan. 5, 1978

[51] Int. Cl.² ............................................. B24B 9/00
[52] U.S. Cl. ....................................... 51/125; 51/128; 51/267; 51/272; 51/377; 403/348
[58] Field of Search ...................... 51/125, 125.5, 128, 51/267, 268, 272, 377, 216 H; 403/348, 349, 353, 335

[56] References Cited

U.S. PATENT DOCUMENTS

| | | | |
|---|---|---|---|
| 2,449,459 | 9/1948 | Eckert | 51/216 H |
| 2,781,618 | 2/1957 | Larson | 51/377 |
| 3,064,400 | 11/1962 | Johnson | 51/267 |
| 3,481,086 | 12/1969 | Paterson | 51/128 |
| 3,574,978 | 4/1971 | Block | 51/377 |
| 3,603,040 | 9/1971 | Paterson | 51/125 |
| 3,650,553 | 3/1972 | Wennstrom | 403/335 X |
| 3,808,746 | 5/1974 | Knecht | 51/128 |
| 3,936,981 | 2/1976 | White | 51/125 |

FOREIGN PATENT DOCUMENTS 86578 7/1921 Fed. Rep. of Germany ........... 403/353

*Primary Examiner*—Harold D. Whitehead
*Assistant Examiner*—Robert P. Olszewski
*Attorney, Agent, or Firm*—Friedman, Goodman & Teitelbaum

[57] ABSTRACT

A dental model trimmer having an easily replaceable abrasive surfaced member. The abrasive surfaced member is contained within a housing and is releasably coupled onto a back plate assembly which is driven by a drive motor. The housing includes a releasably coupled cover plate providing access to the abrasive surfaced member. An opening formed in the cover plate exposes a portion of the abrasive surface so that a dental model workpiece can be inserted into the opening against the abrasive surface to permit work on the dental model workpiece. A tilting work table beneath the opening supports the workpiece during the operation. A stream of water is directed through the front cover onto the abrasive surface and is redirected against this surface by means of baffles positioned inside the cover plate. The opening includes a beveled boundary and an inwardly directed lip permitting angular manipulation of the workpiece, better visibility of the workpiece and maximum safety.

22 Claims, 18 Drawing Figures

4,182,615

DENTAL MODEL TRIMMER

BACKGROUND OF THE INVENTION

This invention relates to material removing devices and more particularly to a dental model trimmer.

In the course of the preparation of a dental model or workpiece, various finishing operations are required to properly complete the model. For example, the model must be ground, finished, and polished. While some of these operations are frequently carried out by hand, dental model trimmers have become available for automated work on such models. By utilizing various types of abrading surfaces, the apparatus can be utilized for abrading, finishing, polishing, grinding, lapping, etc.

One such dental model trimmer is described in U.S. Pat. Nos. 3,481,086 and 3,603,040. In these patents, a housing is provided in which there is contained a grinding wheel driven by a drive motor. An access opening in the front of the housing exposes a portion of the grinding wheel. A work table is positioned in front of the access opening on which the workpiece can be placed during operation of the grinding wheel. The apparatus is supported in a sediment tray and fluid enters the housing and is removed through the sediment tray.

While such dental model trimmer is useful for working on dental models, the apparatus itself is inconvenient to use and prevents efficient operation and manipulation of the workpiece.

For example, it is frequently necessary to change the abrasive surfaced material when it is used up during the course of regular usage. Additionally, even when operating on a single workpiece, it may be necessary to provide different types of abrasive surfaces, as for example different grades of abrasive material or different kinds of abrasive surfaces for grinding, polishing, finishing, etc. Unless an easily provided means is available for quick replacement of the abrasive surface, numerous apparatus must be provided where such replacement in prior art trimmers usually takes twenty to thirty minutes by skilled persons. This becomes costly, and additional trimmers require excessive space.

Additionally, in manipulating the workpiece, the access opening becomes a limiting factor to the efficient use of the apparatus, where the arrangements of prior art devices do not allow the opening to be positioned very close to the abrading surface. By making the access opening excessively large, safety hazards occur, and when the access opening is too small, it becomes difficult to appropriately manipulate the workpiece against the abrading surface. An additional problem concerns the efficient use of the water spray on the abrading surface.

SUMMARY OF THE INVENTION

It is accordingly an object of the present invention to provide a dental model trimmer which avoids the aforementioned problems of prior art devices.

A further object of the present invention is to provide a dental model trimmer which provides for easy and efficient replacement of the abrasive surfaced member, which can be accomplished within a short period of time, requiring no more than a few minutes.

Yet another object of the present invention is to provide a dental model trimmer which includes a housing having a releasably coupled cover plate to permit easy access to the abrasive surfaced member.

A further object of the present invention is to provide a dental model trimmer which includes an abrasive surfaced member releasably coupled onto a support, providing easy replacement of the abrasive surfaced member.

Still a further object of the present invention is to provide a dental model trimmer having an abrasive surfaced member coupled to a backing plate, and including a biasing means for providing ejection of the abrasive surfaced member from the backing plate when the two are separated.

A further object of the present invention is to provide a dental model trimmer having an abrasive surfaced member releasably coupled onto a backing plate assembly, and including a quick release interlocking mechanism for retaining the two in continuous relationship together.

Another object of the present invention is to provide a dental model trimmer which includes a conduit arrangement for directing a flow of water against an abrasive surface, and which includes baffles for redistributing the water onto that surface.

A further object of the present invention is to provide a dental model trimmer which includes a drive motor operating a rotating abrasive surfaced member, and which includes a safety device for locking the motor shaft during replacement of the abrasive surfaced member.

Still a further object of the present invention is to provide a dental model trimmer having a housing in which an abrasive surfaced member rotates, and including an access opening exposing a portion of the abrasive surface and including a beveled boundary with an inwardly directed lip, to provide maximum manipulation of the workpiece and to ensure better visibility of the workpiece and safety during operation.

Yet a further object of the present invention is to provide a dental model trimming system comprising at least two dental model trimming apparatus supported on a common mounting surface, both being operated by a single drive motor.

Briefly, there is provided a dental model trimming apparatus which includes a housing having a main housing member with a rear wall and a perimetric side wall extending therefrom. An aperture is provided in the rear wall. A cover plate is releasably coupled to the front of the main housing member. A drive motor has its output shaft extending through the aperture into the housing. A backing plate assembly disposed in the housing is coupled to the shaft and rotates therewith. An abrasive surfaced member also disposed in the housing is releasably coupled to a front surface of the backing plate assembly and also rotates therewith. An access opening formed in the cover plate exposes a portion of the abrasive surface for contact with a dental model workpiece. A tilting work table is connected to the front of the cover plate adjacent to the access opening so that the workpiece can be placed thereon.

In an embodiment of the invention, a releasable coupling means interconnects the backing plate assembly to the abrasive surfaced member. A biasing means may also be included for biasing the abrasive surfaced member in a direction away from the backing plate assembly, so that the abrasive surfaced member will b ejected from the backing plate assembly upon release of the coupling means. The cover plate also incluues fastening means for a quick-releasable coupling between the cover plate and the main housing member. A sealing member is interposed between the main housing member and the cover plate for providing a water tight arrangement therebetween.

Around the access opening is provided a boundary means including a bounding surface which is beveled in the direction of the abrasive surfaced member, and an inwardly projecting rim extending from the bounding surface into proximate relationship with the abrasive surfaced member. This arrangement ensures maximum visibility of the workpiece and safety while providing for maximum manipulation of the workpiece against the abrasive surfaced member.

Water is supplied through an inlet provided in the cover plate and passes through a conduit to direct the water against the abrasive surfaced member. Baffles perimetrically disposed on the rear surface of the cover plate redirect the water onto the abrasive surfaced member and form an area in which the abrasive surfaced member can be positioned.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the acoompanying drawings of a preferred embodiment in which.

In the various figures of the drawings like reference characters designate like parts.

DETAILED DESCRIPTION OF THE PREFERRED EMBODIMENT

Figure 1:
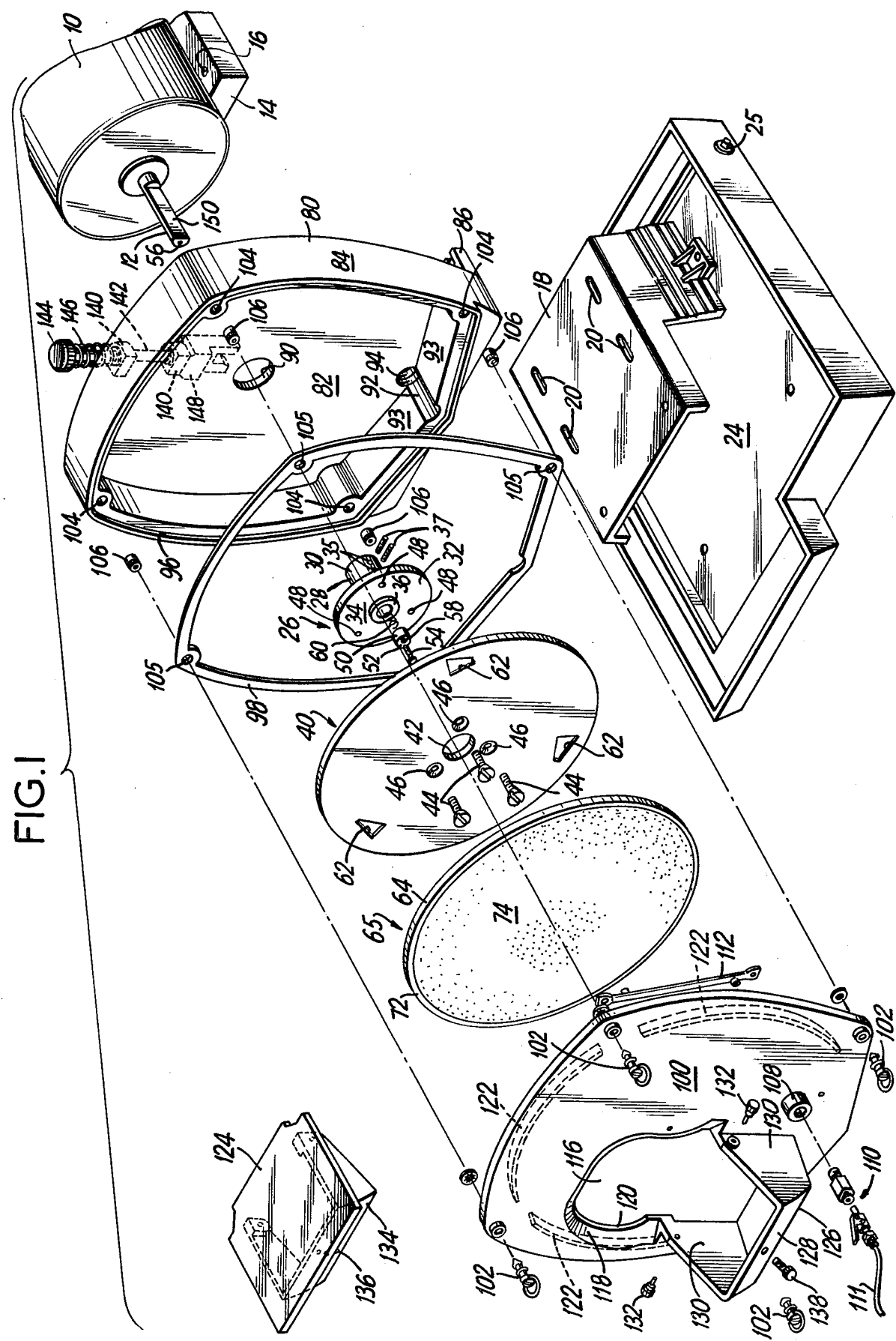
FIG. 1 is an exploded perspective view of the various components of the dental model trimmer according to the present invention.

As illustrated in the drawings, particularly FIGS. 1, 2, 3 and 4, the dental model trimmer comprising the present invention includes a conventional drive motor 10, preferably sealed against the entry of moisture and provided with an outwardly projecting drive shaft 12. Drive motor 10 is provided with conventional mounting means, such as flanges 14 extending from each side of the motor housing. The flanges are provided with apertures 16 for registration with elongated apertures or slots 20 provided in mounting base 18. The drive motor is secured on said mounting base by bolts 22. Resilient means, such as springs or pads, not shown, may be interposed between the motor flanges and the base to prevent vibration as is well known in the art. Mounting base 18 may in turn be secured, by bolts 23, within a sediment tray such as is generally designated by the numeral 24. The sediment tray 24 is provided with a drain plug 25 which is removable for draining the tray, if desired.

It will be understood that the particular form of mounting base and sediment tray illustrated is similar to that described and shown in U.S. Pat. No. 3,603,040 and does not form part of, nor is it essential to this invention. Accordingly, the model trimming device comprising the present invention may be mounted on or in any other form of mounting base and/or tray of conventional design suitable for that purpose.

Drive motor 10 has coupled thereto a backing plate assembly, designated generally by the numeral 26, for rotation therewith. The backing plate assembly comprises a hub member 28 including a sleeve portion 30 provided with a radially extending flange 32. The forward end of the sleeve extends somewhat beyond the forward planar face 34 of the flange 32 forming a forwardly extending locating collar 36. The rear portion of the sleeve portion 30 is provided with two threaded apertures 35 which receive screws 37 to secure the hub member 28 on the motor drive shaft 12. The flange portion of the hub has secured thereto a circular backing plate member 40. The plate member may be formed of any suitable material such as metal or synthetic resin so long as it is capable of providing a rigid planar surface capable of supporting an abrasive disk unit, to be hereinafter described, without distortion during rotation and the application of working pressure by the operator.

It will be noted that the backing plate member is provided with a central aperture 42 of complementary configuration to the perimetric surface of locating collar 36, so that the collar is snugly received within aperture 42 and thus serves to position the backing plate in co-axial relation to the flange 32 and motor drive shaft 12 for concentric rotation therewith. The backing plate member is secured to flange 32 of the hub member 28 by means of screws 44 which extend through counterbored apertures 46 into threaded openings 48 provided in the flange.

The hub 28 may further be provided, if desired, with a spring biased ejection arrangement adapted to maintain the abrasive disk unit, to be hereinafter described, under a degree of pressure and to facilitate the removal of such unit preparatory to replacement by another. As may be seen more particularly from FIGS. 1 and 4, a plunger 50 is provided in the form of a hollow cylindrical cup having a transverse wall or cap 52 at one end thereof. The plunger 50 is slideably disposed within the bore of the hub sleeve portion 30 adjacent the end of the motor drive shaft 12 which is secured within said sleeve portion. The cap end of the plunger 50 is provided with a counterbore 58 to receive the head end of retaining screw 54 which extends through an aperture in the cap and is received in a threaded axial bore 56 provided in the forward end face of the motor drive shaft.

It will be noted that the axial extent of the counterbore 58 in the plunger cap is greater than the axial extent of the head of the screw 54 so that the plunger may be axially displaced in a direction remote from the shaft. The plunger is urged to this displacement by means of a compression spring 60 disposed within the hollow interior of the cylindrical plunger and around the shank of the screw 54. One end of the spring 60 bears against the forward end face of the motor drive shaft 12 while the other end thereof bears against the interior surface of the plunger cap, thereby resiliently biasing the plunger outwardly against an abrasive disk unit, as will more fully be described hereafter below.

Figure 2:
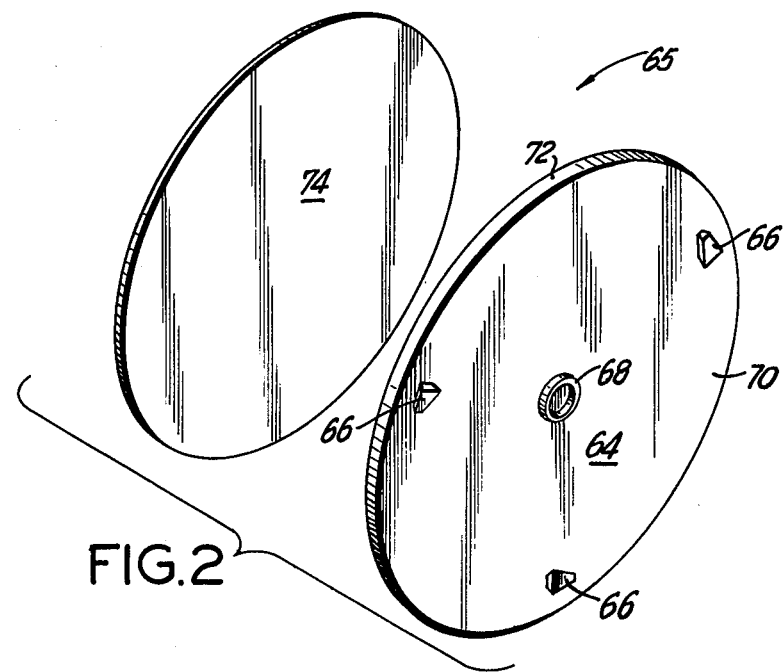
FIG. 2 is an exploded perspective view showing the rear surfaces of the abrasive support disk and the abrasive surfaced member.
Figure 3:
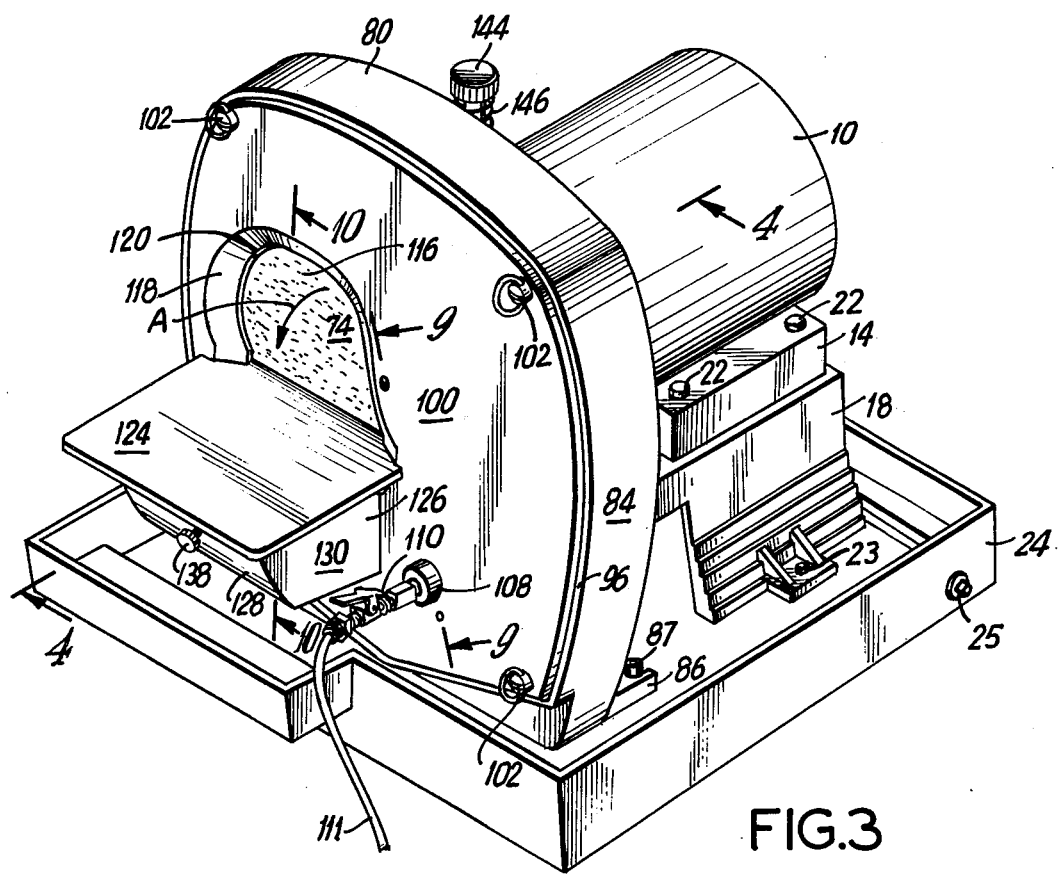
FIG. 3 is a perspective view of the assembled dental model trimmer.

Backing plate 40 is also provided with a plurality of tapered dovetail mortise like apertures 62, as shown in FIG. 1, for receiving essentially complementary tapered dovetail tenon-like bosses 66, as shown in FIG. 2, formed on the abrasive carrier disk units 65 adapted to be mounted thereon. The apertures 62 extend through the body of the backing plate member 40 and are spaced apart circumferentially about the rotational axis of the backing plate 40.

Figure 5:
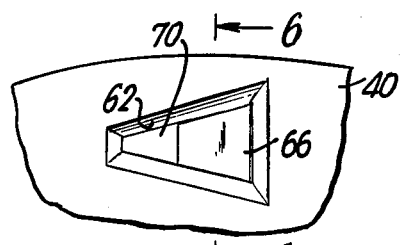
FIG. 5 is a fragmentary rear view of the backing plate showing a boss of the abrasive support disk extending through an aperture of the backing plate.
Figure 6:
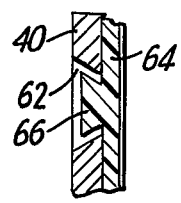
FIG. 6 is a side sectional view taken along line 6—6 of FIG. 5.

As heretofore indicated, the backing plate is adapted to receive and support interchangeable abrasive disk units 65 for use in the performance of trimming dental casts or models as well as in the performance of other dental related operations. In the preferred form of the present invention herein set forth, the interchangeable abrasive disk unit comprises a support disk 64 which carries on its front surface an abrasive surfaced material, the back or reverse surface 70 of the disk being provided with the bosses 66 as heretofore described. It should be noted that these bosses are configured so that they are complementary to and provide mating engagement with the narrow ends of the apertures 62 of the backing plate. The wider ends of the bosses are shorter than the wider ends of the apertures in a circumferential direction so that the bosses may be freely inserted into the apertures at the wider end of the latter, as shown in FIGS. 5 and 6, where FIG. 5 shows the rear surface of the backing plate 40.

Figure 4:
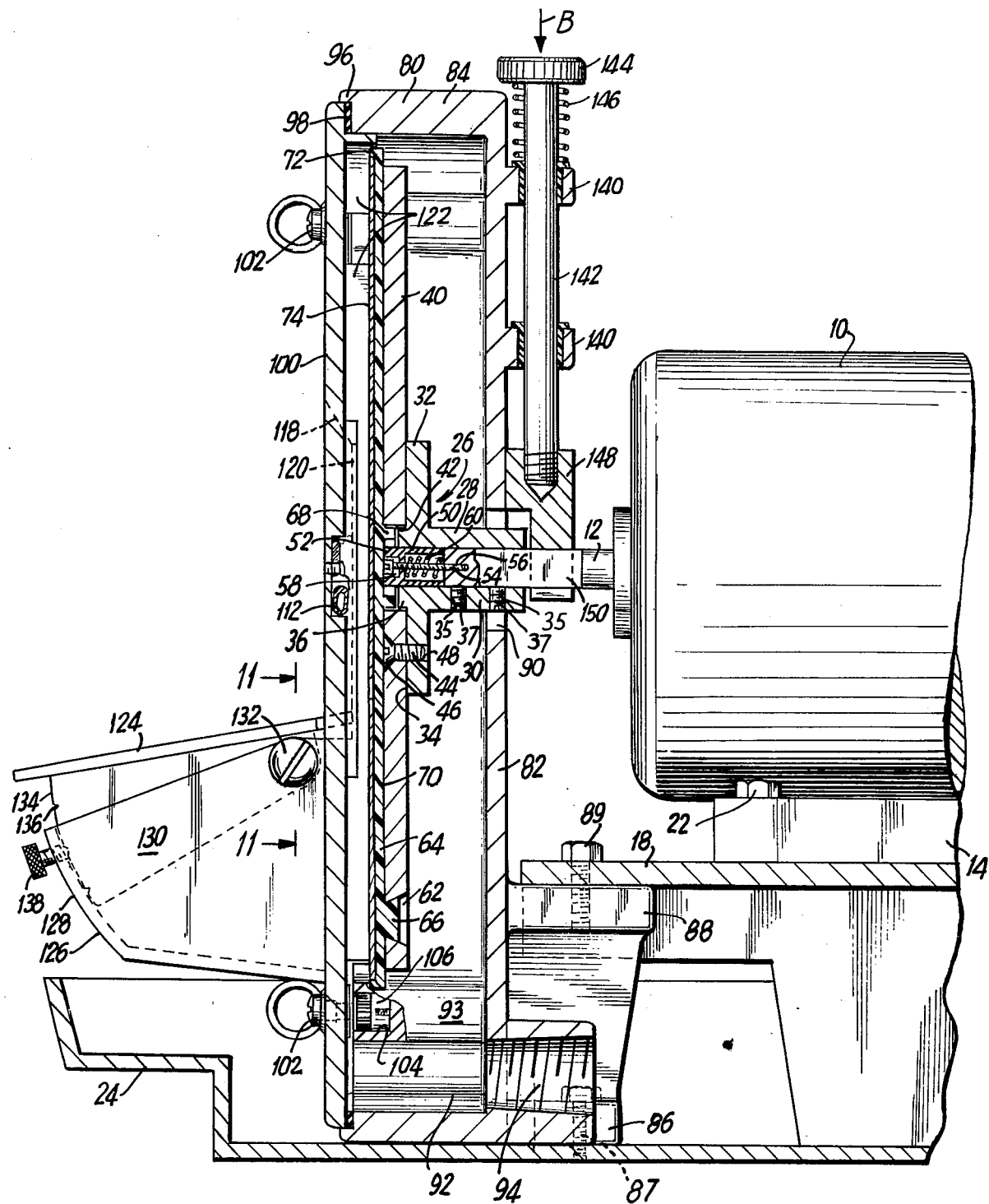
FIG. 4 is a side sectional view taken along the line 4—4 of FIG. 3.
Figure 7:
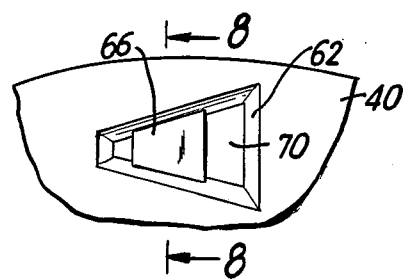
FIG. 7 is a fragmentary rear view of the backing plate showing a boss of the abrasive support disk locked in an aperture of the backing plate.
Figure 8:
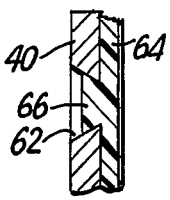
FIG.8 is a sectional view taken along line 8—8 of FIG. 7.

Upon the rotation of the disk and plate with respect to each other, the disk 64 is rotated so that the bosses are rotated into the narrow ends of the apertures, and thus are wedgingly engaged with the walls of the apertures 62 in the dovetail fashion, as shown in FIGS. 7 and 8. Accordingly, the parts are simultaneously drawn into close contact with each other so that the backing plate 40 will act as a rigid planar backing for the support disk unit 65 and will be effectively coupled for rotation therewith, as shown in FIG. 4. In order to facilitate the location of the support disk with reference to the backing plate, a raised locating collar 68 is provided in the reverse surface 70 of support disk 64.

The raised collar 68 is dimensioned so as to be snugly received in the central aperture 42 of backing plate 40 so that it will be accurately located for concentric rotation with respect to the axis of the plate 40, hub member 28 and motor drive shaft 12. It should be noted, in this respect, that the thickness of the backing plate 40 exceeds the height of the locating collar 36 on hub member 28 so that the support disk collar 68 may also be received in and accurately located in the aperture 42 of the backing plate 40.

FIG. 12–16 show a modified engagement between the backing plate and the abrasive support disk, which functions in the same manner as the above-mentioned engagement therebetween. The modified backing plate 40A is provided with a central aperture 42A and counterbored apertures 46A for the same purpose these apertures were provided in the backing plate member 40, set forth above, to receive the locating collar 36 and the screws 44 respectively. The modified support disk 64A is also provided with a raised collar 68A on the reverse surface 70A so as to be snugly received in the central aperture 42A of the backing plate 40A.

The modifications include the backing plate 40A being provided with a plurality of tapered dovetail mortise like apertures 62A for receiving essentially complementary tapered bosses or projections 66A formed on the support disk 64A adapted to be mounted thereon. The apertures 62A are provided in recesses 63 formed on the rear surface of the backing plate 40A so that the combined openings formed thereby extend through the body of the backing plate member 40A and are spaced apart circumferentially about the rotational axis of the backing plate 40A. Additionally, an enlarged opening 67 is provided at one end of each aperture 62A to form a keyhole arrangement.

Figure 13:
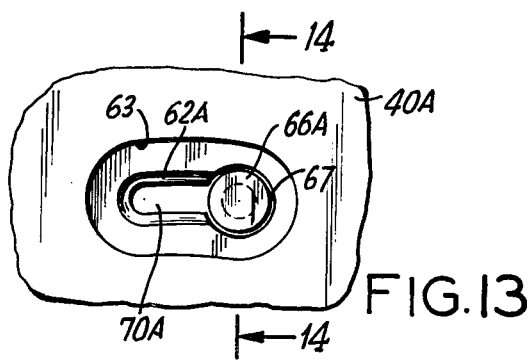
FIG. 13 is a fragmentary view of a modified backing plate of FIG. 12 showing a boss of a modified abrasive support disk extending through an aperture of the backing plate.
Figure 14:
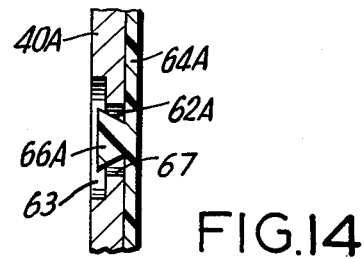
FIG. 14 is a side sectional view taken along line 14—14 of FIG. 13.

The bosses 66A are configured so that they are complementary to and provide mating engagement with the narrow ends of the aperture 62A of the backing plate, preferably, these narrow ends being slightly inclined towards each other to be narrower than the main portion of the apertures to provide a tighter fit with the bosses 66A. Accordingly, the bosses 66A are smaller than the enlarged openings 67 so that the bosses may be freely inserted into these openings as shown in FIGS. 13, 14, where FIG. 13 shows the rear surface of the backing plate 40A.

Figure 15:
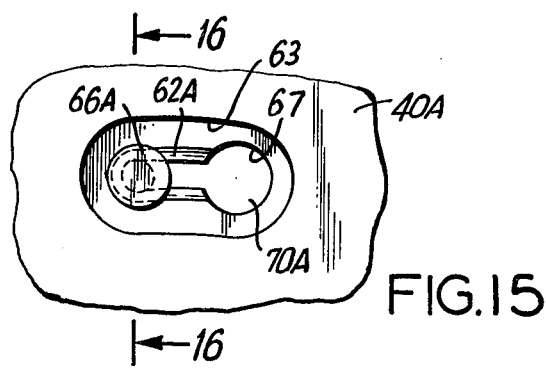
FIG. 15 is a fragmentary view of the modified backing plate of FIG. 12 showing a boss of the modified abrasive support disk locked in an aperture of the backing plate.
Figure 16:
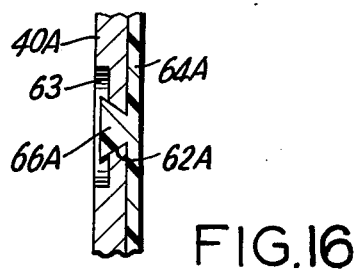
FIG. 16 is a side sectional view taken along line 16—16 of FIG. 15.

Upon the rotation of the disk and plate with respect to each other, the disk 64A is rotated so that the bosses are rotated into the narrow ends of the apertures 62A, and thus are wedgingly engaged with the walls of the apertures 62A in dovetail fashion, as shown in FIGS. 15 and 16. Thus, the parts are simultaneously drawn into close contact with each other so that the backing plate 40A will act as a rigid planar backing for the support disk 64A and will be effectively coupled for rotation therewith, in the same manner as set forth above. It should be noted that the thickness of the backing plate 40A is the same as that of the former backing plate 40, to function in the same manner as set forth above.

Abrasive support disk 64 or 64A is advantageously formed of a low cost synthetic resin, such as by injection molding a plastic material, and is intended to be disposable. The obverse of the disk presents a planar surface surrounded by a slightly projecting circumferential lip 72 or 72A. The support disk carries an abrasive surfaced material suitable for model trimming and other dental operations. It has been found advantageous to apply the abrasive in the form of a paper or cloth sheet 74 cut to circular form so that it fits readily into the recessed planar area defined by lip 72 or 72A. The paper or cloth sheet 74 is provided with a deposit of suitable abrasive material on one surface thereof and a coating of a pressure sensitive adhesive on the other. The abrasive surfaced sheet 74 is adhered to the support disk 64 or 64A by contact with the pressure sensitive adhesive surface.

Sheets of abrasive surfaced material provided with pressure sensitive adhesive backings and capable of being used under wet or dry conditions are conventional and commercially available, being suitable for use in a wide variety of trimming, finishing and polishing operations. The term "abrasive" as herein used is intended to encompass all varieties of surface treating coatings such as abrading, finishing, polishing and lapping materials which are suitable to be provided on the support disk 64 or 64A. It is also to be noted that the abrasive support disk may be provided with an abrasive surface, as herein defined, directly on the obverse face thereof as by treating the surface or depositing a layer of abrasive material directly thereon.

As heretofore described, the abrasive support disks 64, 64A may be readily engaged or disengaged from backing plate 40, 40A, respectively, by merely rotating them toward or away from each other respectively, as set forth above.

The model trimming arrangement heretofore described is enclosed in a housing comprised of a main housing member 80 which comprises a pan shaped open face enclosure having a planar rear wall 82 and a perimetric side wall 84 extending therefrom. Extending from the back of the rear wall is a pair of slotted mounting legs 86 which are bolted by bolts 87 to a support such as the sediment tray 24. Further securement of the main housing member is accomplished by a pair of rearwardly extending mounting lugs 88 formed integrally on the outer surface of the rear wall 82 and bolted by bolts 89 to mounting base 18. The rear wall 82 is also provided with a generally centrally disposed aperture 90 through which the drive shaft 12 of the motor and the hub carried thereby extend into the interior of the housing, as shown in FIG. 4.

The main housing member is further provided with a drainage port 92 at the point of convergence of the downwardly slanted bottom portions 93 of the perimetric wall. The drainage port 92 includes a rearwardly extending exit tube 94 which is suitably threaded for connection to further drainage elements if desired. The perimetric side wall 84 is provided with a recessed lip as shown at 96 for receiving a sealing gasket 98.

The enclosure of the open face of the main housing member 80 is accomplished by means of a cover plate 100 which is provided with the stud portions 102 of quarter turn type fasteners. It will be noted that the main housing member is provided with openings 104 at the corners thereof wherein the spring loaded receptacle portions 106 of the fasteners 102 are securely press fitted. Fasteners may be of the type commercially available from Southco, Inc. of Concordville, Pa., under the catalog designation No. 82. It will be seen that the cover plate may be readily secured and disengaged from the main housing member by the operation of the quarter turn fasteners and that a water tight seal is accomplished by the interposition of the sealing gasket, which is provided with corner openings 105 for receiving the fasteners 102. The fasteners, being spring loaded, cause a resilient pressure to be applied to the sandwiched gasket, permitting the cover to be removed and replaced repeatedly while maintaining the integrity of the gasket.

Figure 9:
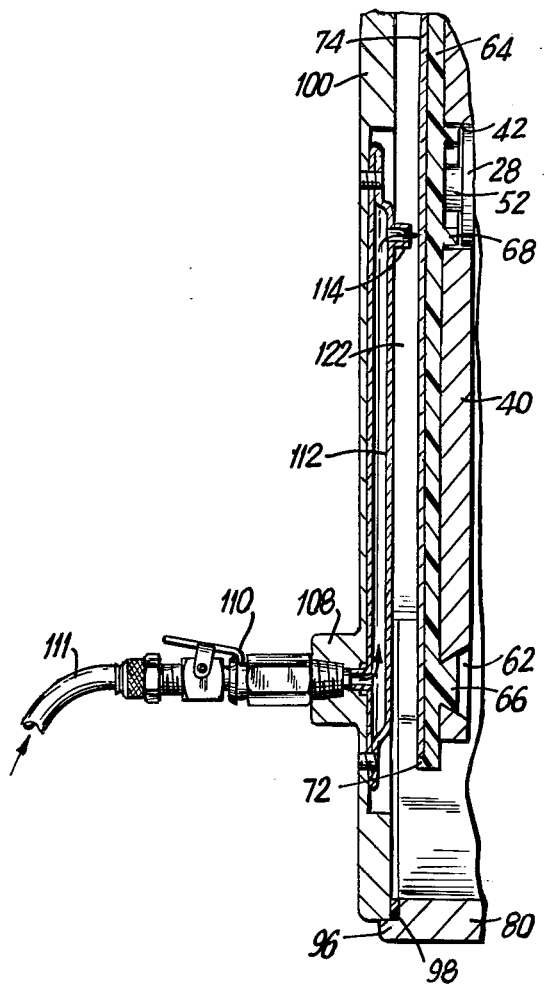
FIG. 9 is a side sectional view of the water supply system taken along line 9—9 of FIG. 3.

The cover plate further carries the water supply means for maintaining a constant spray of water against the abrasive surface. As may be seen from FIGS. 1, 3 and 9, a water inlet 108 is provided in the body of the cover plate, the external end of which is provided with a quick disconnect fitting 110 for rapid attachment and detachment of a water supply hose 111 therefrom. The interior opening of the water inlet communicates with a tubular conduit 112 which rests in a radially extending channel formed in the interior surface of the cover plate. The discharge end 114 of the conduit is disposed so as to direct a stream of water against the abrasive surface in the central region of the disk 74.

The cover plate is further provided with a workpiece access opening 116 disposed to one side of the central axis of rotation. The direction of the rotation being indicated by the arrow A shown in FIG. 3. The opening is configurated as indicated by the drawings and dimensioned so as to provide a maximum area of abrasive surface exposure. It is a significant feature of the present invention that bounding surfaces of the opening are bevelled in the direction of the abrasive disk as shown at 118, thus increasing the operative area and permitting angular manipulation of the workpiece. Maximum visibility and safety are provided since the open space between the lip of the access opening and the abrasive surface is thus minimized. Further reduction of the open space is accomplished by an inwardly projecting rim 120 of the access opening formed on the interior surface of the cover plate. The interior surface of the cover plate is also provided with baffles 122. It will be noted that the abrasive disk and backing plate assembly may be moved into close proximity to the interior surface of the cover plate and within the area defined by the baffles. As a consequence of this, the abrasive surface may be brought very close to the access opening. As the disk throws water outwardly by centrifugal force during rotation, such water is redirected by the baffles against the disk which results in a highly efficient operation.

Figure 10:
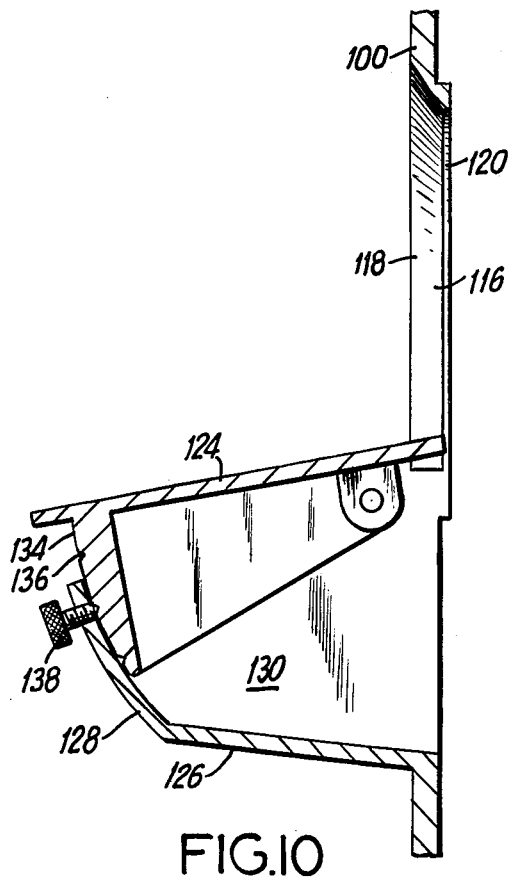
FIG. 10 is a side sectional view through the access opening taken along line 10—10 of FIG. 3.
Figure 11:
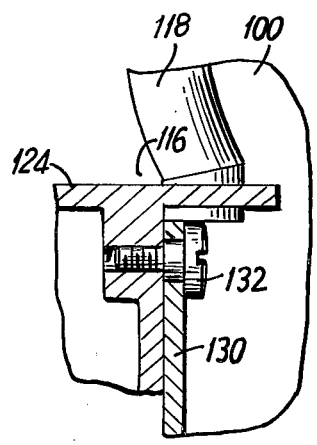
FIG. 11 is a sectional view of the pivoting arrangement of the work table taken along line 11—11 of FIG. 4.
Figure 12:
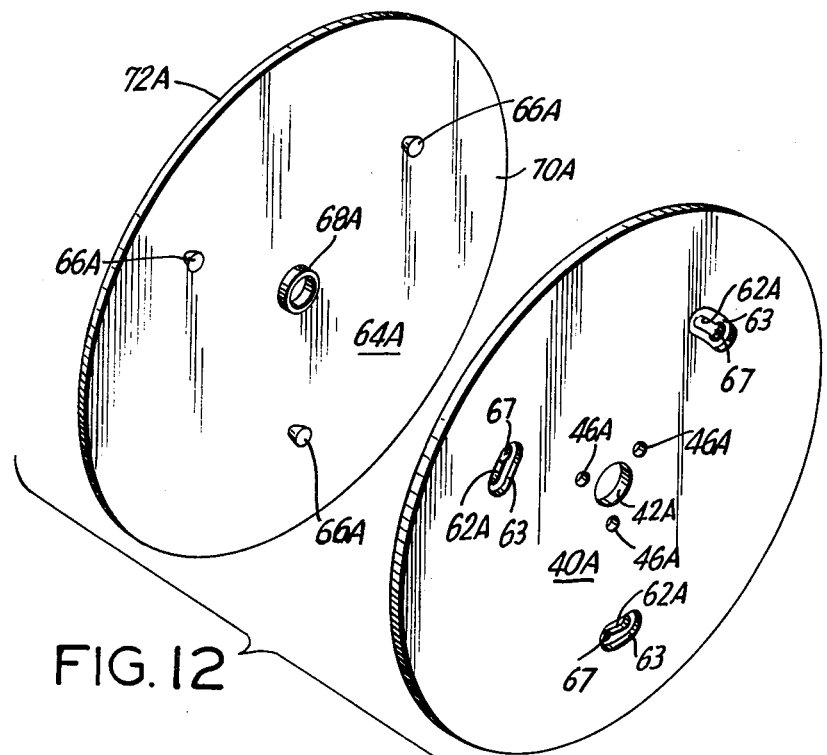
FIG. 12 is a perspective view showing rear surfaces of a modified backing plate and a modified abrasive support disk.

Along the bottom edge of the access opening 116 there is provided a tilting work table 124, as may be additionally seen from FIG. 10. The work table 124 is mounted on a support body 126. The support body 126 is formed by deflecting a portion of the cover plate 100 to provide front, bottom and side walls. Front wall 128 is formed in an arc. The work table is hinged to the side walls 130 of the support body 126 by means of shoulder screws 132, as shown in FIG. 11. The under surface of the work table is provided with depending side walls and an arcuate front wall 134, all of which are configurated to be nestably received within the confines of the support body walls. The planar portion of the table extends beyond the confines of the support body walls, permitting it to rest thereon when desired. The front wall 134 of the work table presents a curved surface similar to the curvature of the support front wall 128 and is provided with a series of dimples in its surface as shown at 136 in FIGS. 4 and 10. A threaded set screw 138, carried by front wall 128, may be engaged in and tightened against any one of these dimples 136 to provide for secure maintenance of the work table at any desired angle with respect to the plane of the abrasive disk.

It will be seen from the foregoing that an arrangement is provided for a highly efficient and safe dental trimming device. Furthermore, that the abrasive disk may be replaced or interchanged with other disks in a simple and rapid manner.

As a further feature for facilitating replacement of the abrasive disk assembly, an arrangement is provided for locking the motor shaft 12 and backing plate 40 or 40A mounted thereon against rotation as the abrasive disk assembly is being changed. This arrangement may be seen in FIGS. 1 and 4. The back of the main housing member 80 is provided with a pair of bearing guide members 140 within which a rod 142 is slideably disposed. The upper end of rod 142 is provided with a cap member 144, and a compression spring 146 is confined between the cap and the upper bearing guide biasing the rod to an elevated position. The lower end of the rod 142 is provided with a yoke member 148 provided with an opening in line with drive motor shaft 12. It will be noted that the shaft 12 is provided with a flat surface 150, and that the yoke member is dimensioned so as to straddle the flattened shaft and hold it against rotation when the slide rod 142 is moved downwardly. Thus, the manual depression of the rod 142 in the direction of arrow B shown in FIG. 4 will cause the shaft to be locked and held against movement during change of abrasive disks, as long as the rod 142 is depressed. It is noted, that during the above replacement, the motor 10 is off, where the biasing of the spring 146 is a safety feature to insure that the yoke member 148 is in its normal elevated unengaging position when the motor is turned on.

Figure 17:
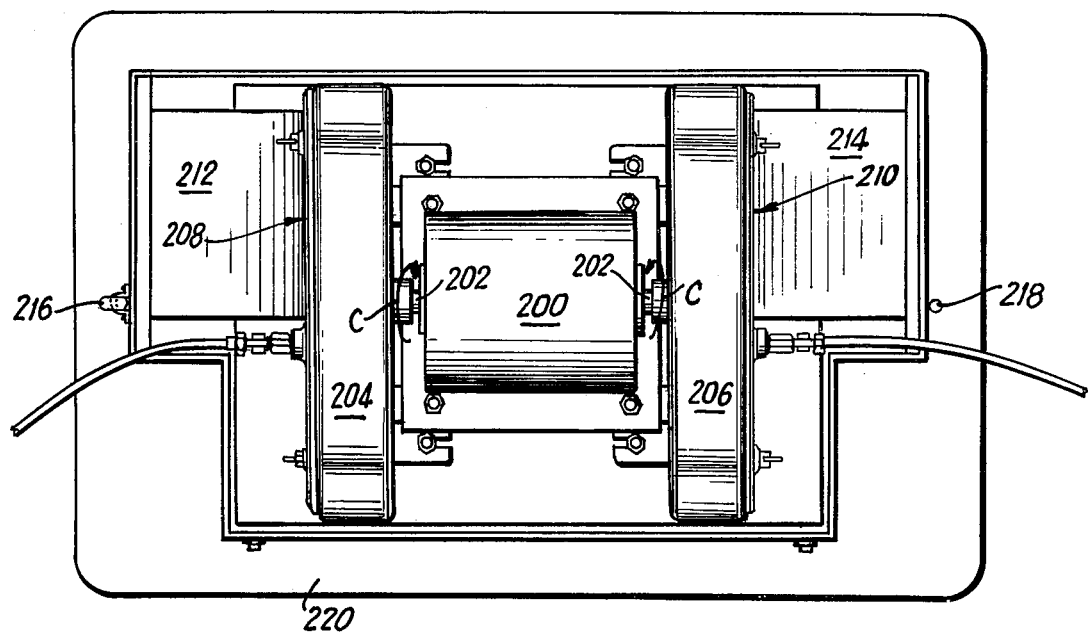
FIG. 17is a top plan view of an embodiment of the present invention having two work stations.
Figure 18:
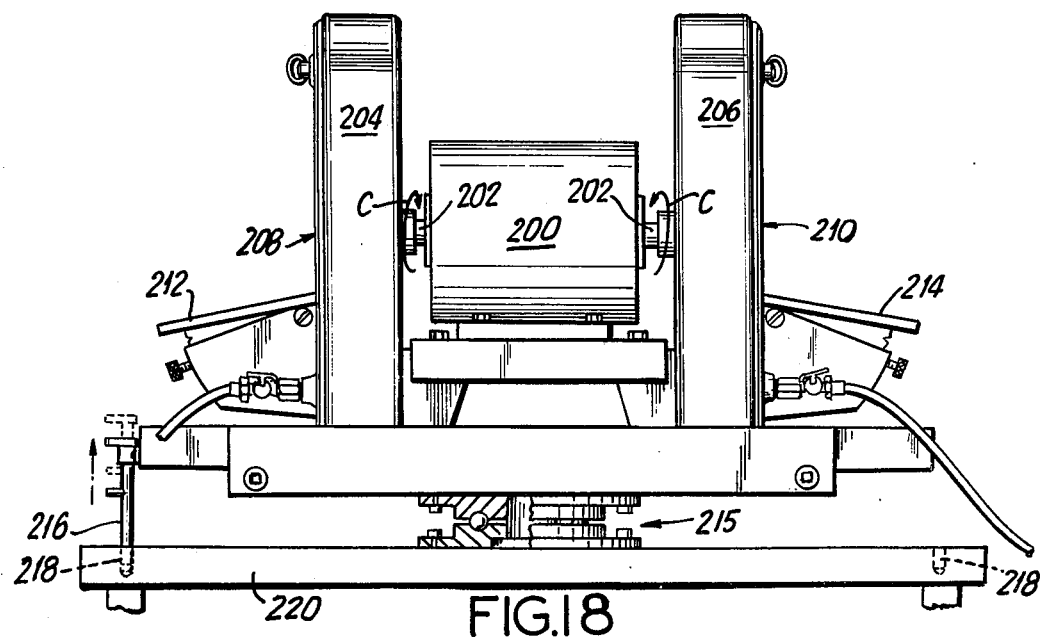
FIG. 18 is a side elevational view of the embodiment shown in FIG. 17.

FIGS. 17 and 18 illustrate a form of the present invention wherein a single motor drive unit is used to operate two model trimming work stations so that the device may be simultaneously used by two operators in an economical and efficient manner. Furthermore, the arrangement permits the device to be set up to operate with different grades of abrasive disk so that the operator may have different grades available to him by merely selecting the working head he desires to use. FIGS. 17, 18 illustrate a drive motor 200 having a drive shaft 202 extending from both ends of the motor. The numerals 204 and 206 designate housings within which there is disposed the trimming arrangement all as heretofore described. It should be noted however, that the housings are so arranged that their workpiece access openings 208 and 210 respectively, expose the portions of each abrasive disk rotating in the arrow direction C toward the tilting tables 212 and 214 respectively. This assures that a workpiece positioned on either table will be urged toward the table as the abrasive disk operates upon it, as a safety feature to avoid the workpiece from being forced upwardly out of the operator's hand.

A further improvement is shown in FIGS. 17 and 18, where the arrangement may be mounted upon a bearing 215 for permitting the whole arrangement to be rotated upon a vertical axis. This arrangement permits the operator to use either end of the device without changing his operating position. In order to maintain the device in fixed position during operation, a vertically reciprocable locking pin 216 is provided. The pin is reciprocably secured to the unit, the lower end being received in either of the openings 218 provided in a supporting table 220. When the pin is elevated to the broken line position, the entire unit may be swung around to the alternate position.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental model trimmer comprising:

a housing including a main housing member having a rear wall and a perimetric side wall extending therefrom, with an aperture provided in said rear wall, and a cover plate releasably coupled to said main housing member;

sealing means interposed between said main housing member and said cover plate for providing a water tight arrangement therebetween, said sealing means including a sealing gasket, said perimetric side wall further including a recessed lip for receiving said sealing gasket thereagainst;

fastening means for releasably coupling said cover plate to said main housing member, said fastening means including spring loaded quarter turn fasteners extending through a front surface of said cover plate and into receptacles provided in said recessed lip of said perimetric side wall so that resilient pressure is applied to said sealing gasket providing said water tight arrangement;

a drive motor having an output shaft extending through said aperture and into said housing;

a backing plate assembly within said housing and coupled to said output shaft for rotation therewith;

an abrasive surfaced member in said housing between said cover plate and said backing plate assembly, said abrasive surfaced member being spaced from said output shaft;

releasable coupling means for coupling said backing plate assembly to said abrasive surfaced member for rotation therewith, said releasable coupling means including a plurality of apertures in said backing plate assembly and a correspondingly plurality of complementary bosses on said abrasive surfaced member, said apertures and bosses being respectively spaced apart circumferentially about a common rotational axis of said backing assembly and said abrasive surfaced member, said bosses and apertures matingly engaging and interlocking to rigidly retain said abrasive surfaced member against said backing plate assembly;

an access opening provided in said cover plate to expose a portion of an abrasive surface of said abrasive member to a dental model workpiece;

boundary means provided around said access opening for permitting angular manipulation of the workpiece and better visibility of the workpiece, said boundary means including a bounding surface beveled in a direction of said abrasive surfaced member and an inwardly projecting rim extending from said bounding surface into proximate relationship with said abrasive surfaced member; and a tilting work table connected to said cover plate adjacent to said access opening on which the workpiece can be placed;

whereby the spacing of said abrasive surfaced member from said output shaft permits said abrasive surfaced member to be positioned closer to said access opening in said cover plate for better control of the workpiece while working thereon.

2. A dental model trimmer as in claim 1, wherein each of said apertures of said backing plate assembly has a mortise-like cross sectional configuration with side walls converging towards the abrasive surfaced member, and a trapezoidal planar configuration with a wider leading end and a narrow trailing end, with respect to the direction of rotation; each of said bosses having a complementary tenon-like cross sectional configuration with diverging side walls corresponding to the converging side walls of the apertures, and a planar configuration corresponding to a portion of said trapezoidal configuration extending from its narrow end, whereby the bosses can be inserted into the wider leading end of the apertures and upon relative rotation of the backing plate assembly and abrasive surfaced member, the bosses move into the narrow trailing ends of the apertures and wedgingly engage the side walls of the apertures in dovetail fashion.

3. A dental model trimmer as in claim 1, wherein each of said apertures of said backing plate assembly has a mortise-like cross sectional configuration with side walls converging towards the abrasive surfaced member, each of said bosses being a tapered projection having a complementary cross sectional configuration with diverging side walls corresponding to the converging side walls of the apertures, whereby the projections wedgingly engage the side walls of the apertures in dovetail fashion.

4. A dental model trimmer as in claim 3, wherein each of said apertures of said backing plate assembly has an enlarged opening at a leading end with respect to the direction of rotation to provide a keyhole arrangement, each said enlarged opening being larger in diameter than said projections, whereby said projections can be inserted into the enlarged opening and upon relative rotation of the backing plate assembly and the abrasive surfaced member, the projections move into narrow trailing ends of the paertures and wedgingly engage therein.

5. A dental model trimmer as in claim 3, wherein each of said apertures of said backing plate assembly extends from an associated recess provided in a front surface of the backing plate assembly to a rear surface thereof, said projections being longer than length of said apertures with top portions of said projections being located within the recesses when in an engaged position.

6. A dental model trimmer as in claim 1, and further comprising biasing means for biasing said abrasive surfaced member in a direction away from said backing plate assembly, whereby said abrasive surfaced member is ejected from said backing plate assembly upon release of said coupling means.

7. A dental model trimmer as in claim 6, wherein said biasing means comprises an axially displaceable plunger means extending from a remote end of said shaft and bearing against said abrasive surfaced member, spring means disposed with respect to said plunger means for resiliently biasing the plunger means against said abrasive surfaced member and capable of axially displacing it, and limiting means for limiting the axial displacement of said plunger means.

8. A dental model trimmer as in claim 1 and further comprising a water inlet means in said cover plate, a tubular conduit disposed on an interior surface of said cover plate and having its input end in fluid flow communication with said water inlet means and its discharge end disposed adjacent said abrasive surfaced member for directing a stream of water thereagainst, and a drainage port provided in said main housing member for discharging the water.

9. A dental model trimmer as in claim 8, wherein the bottom section of said perimetric side wall comprises downwardly converging transverse portions, said drainage port located at the point of convergence of said transverse portions.

10. A dental model trimmer as in claim 8, and further comprising baffle means perimetrically positioned on the interior surface of the cover plate and outwardly of said abrasive surfaced member, said abrasive surfaced member being positioned within an area defined by said baffle means.

11. A dental model trimmer as in claim 1 and further comprising a support body formed on said cover plate beneath said access opening, hinge means for hingedly connecting said work table to said support body, and adjusting means for adjustably positioning the work table with respect to said support body.

12. A dental model trimmer as in claim 11, wherein said support body is formed by a deflected portion of the cover plate to provide front, bottom and side walls, said front wall being arcuate in cross section; said work table comprising front, and side walls and a planar top, the front wall of the work table being of arcuate shape corresponding to the front wall of the support body, whereby said work table can be nestably secured within the confines of the support body, and wherein said hinge means couples the side walls of the work table to the side walls of the support body.

13. A dental model trimmer as in claim 12, wherein said adjusting means comprises a series of recesses in the front wall of said work table, and a set screw extending through the front wall of said work table and engaging a selected one of the recesses.

14. A dental model trimmer as in claim 1, wherein said backing plate assembly comprises a hub member and a circular backing plate member, said hub member further comprising a radially extending flange, a sleeve axially extending on one side thereof, and a coaxially located collar on the other side thereof, said sleeve connected onto said shaft, said backing plate member having a central aperture for receiving said collar, and fastening means for securing said backing plate member onto said flange.

15. A dental model trimmer as in claim 14, wherein said abrasive surfaced member comprises a support disk having an axially projecting circumferential lip and a coaxially extending disk collar, said abrasive surface being provided on said support disk within the area defined by said circumferential lip, said central aperture of said backing plate member receiving said disk collar, and wherein said backing plate member is of a thickness greater than the axial extent of said locating collar and of said disk collar.

16. A dental model trimmer as in claim 15, wherein said abrasive surface comprises a sheet having abrasive material on one side thereof and pressure sensitive adhesive on the other side thereof.

17. A dental model trimmer as in claim 15 and further comprising a plunger including a hollow cylindrical cup having a cap at one end thereof, said plunger slidably disposed within said sleeve of said hub member a counterbore in said cap, a retaining screw extending through said cup into the shaft of said drive motor, and head of said screw maintained in said counterbore, the axial extent of said counterbore being greater than the axial extent of the screw head whereby the plunger may be axially displaced in a direction remote from the shaft, and compression spring means disposed in said cup for resiliently biasing said plunger outwardly from said shaft and against said support disk.

18. A dental model trimmer as in claim 1 and further comprising a mounting base supporting said housing and said drive motor, and a sediment tray receiving said mounting base.

19. A dental model trimmer as in claim 1 and further comprising locking means to lock said motor output shaft and said backing plate assembly against rotation relative to said main housing member for permitting said abrasive surfaced member to be rotated relative to said backing plate assembly in order to engage and disengage said bosses on said abrasive surfaced member to and from said apertures in said backing plate assembly when mounting and removing said abrasive surfaced member.

20. A dental model trimmer as in claim 19, wherein said locking means comprises bearing guide means disposed on an outside surface of said rear wall, a rod slidably disposed for radial movement within said bearing guide means, cap means disposed on a remote end of said rod, compression spring means confined between said cap means and said bearing guide means for biasing said rod away from said motor shaft, a yoke member disposed on an opposite end of said rod, said yoke being aligned with said rear wall aperature to straddle said motor shaft, said motor shaft having a D-shaped cross section.

21. A dental model trimmer as in claim 1 in combination with a second dental model trimmer, wherein said output shaft extends outwardly from both ends of said drive motor, said first mentioned and second dental model trimmers both being coupled to respective ends of said output shaft to provide first and second trimmer work stations with said abrasive surfaced member of said first mentioned dental model trimmer facing in one direction and an abrasive surfaced member of said second dental model trimmer facing in an opposite direction, said output shaft rotating both of said abrasive surfaced members of said first mentioned and second dental model trimmers in a direction towards a bottom of said access opening provided in said first mentioned dental model trimmer and a bottom of an access opening provided in said second dental model trimmer respectively, and a common mounting base supporting said drive motor and both said first mentioned and second dental model trimmer.

22. A dental model trimmer in combination with a second dental model trimmer as in claim 21, wherein said mounting base includes means for rotating said first mentioned and second dental model trimmers between said first and second trimmer work stations, and means for releasably locking said first mentioned and second dental model trimmers at one of said two stations during operation thereof.

* * * * *